(12) United States Patent
Blei et al.

(10) Patent No.: US 10,473,511 B2
(45) Date of Patent: Nov. 12, 2019

(54) SENSOR DEVICE FOR ATTACHMENT TO A DRUG DELIVERY DEVICE

(71) Applicant: Sanofi-Aventis Deutschland GmbH, Frankfurt am Main (DE)

(72) Inventors: Gertrud Blei, Jena (DE); Alexander Allerdings, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 338 days.

(21) Appl. No.: 14/783,092

(22) PCT Filed: Apr. 16, 2014

(86) PCT No.: PCT/EP2014/057774
§ 371 (c)(1),
(2) Date: Oct. 8, 2015

(87) PCT Pub. No.: WO2014/173767
PCT Pub. Date: Oct. 30, 2014

(65) Prior Publication Data
US 2016/0047685 A1 Feb. 18, 2016

(30) Foreign Application Priority Data
Apr. 22, 2013 (EP) .................................... 13164746

(51) Int. Cl.
*G01F 23/292* (2006.01)
*G01N 21/55* (2014.01)
(Continued)

(52) U.S. Cl.
CPC ....... *G01F 23/292* (2013.01); *A61M 5/31551* (2013.01); *G01N 21/55* (2013.01);
(Continued)

(58) Field of Classification Search
CPC .................. G01F 23/292; G01N 21/55; G01N 2201/062; G01N 2201/08; G06K 9/00456;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 102427840 | 4/2012 |
| CN | 102725011 | 10/2012 |

(Continued)

OTHER PUBLICATIONS

International Search Report and Written Opinion in International Application No. PCT/EP2014/057774, dated May 20, 2014, 12 pages.

(Continued)

*Primary Examiner* — John R Lee
(74) *Attorney, Agent, or Firm* — Fish & Richardson P.C.

(57) ABSTRACT

A sensor device configured to be attached to a drug delivery device and configured to illuminate the drug delivery device when attached, the sensor device comprising: a light guide having a first surface, a second surface opposed to the first surface, at least one side surface extending between the first and second surfaces and a light out-coupling structure configured to cause diffuse light to be emitted from the first surface when light is input into the light guide; at least one light source configured to in-couple light into the light guide; and an optical sensor arranged to receive light reflected from a surface of the drug delivery device.

14 Claims, 10 Drawing Sheets

(51) Int. Cl.
*G06K 9/00* (2006.01)
*G06T 11/00* (2006.01)
*A61M 5/315* (2006.01)
*A61M 5/31* (2006.01)

(52) U.S. Cl.
CPC .......... *G06K 9/00456* (2013.01); *G06T 11/00* (2013.01); *A61M 5/3157* (2013.01); *A61M 5/31568* (2013.01); *A61M 2005/3126* (2013.01); *A61M 2205/3306* (2013.01); *A61M 2205/50* (2013.01); *A61M 2205/52* (2013.01); *G01N 2201/062* (2013.01); *G01N 2201/08* (2013.01)

(58) Field of Classification Search
CPC ............... G06T 11/00; A61M 5/31551; A61M 5/31568; A61M 5/3157; A61M 2005/3126; A61M 2205/3306; A61M 2205/50; A61M 2205/52
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,376,785 A * | 12/1994 | Chin | G01D 5/30 250/214 PR |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,697,699 A * | 12/1997 | Seo | F21V 5/02 235/462.42 |
| 5,792,117 A * | 8/1998 | Brown | A61B 5/14532 235/462.04 |
| 5,921,966 A | 7/1999 | Bendek et al. | |
| 5,961,495 A | 10/1999 | Walters et al. | |
| 5,963,333 A | 10/1999 | Walowit et al. | |
| 6,004,297 A | 12/1999 | Steenfeldt-Jensen et al. | |
| 6,020,583 A * | 2/2000 | Walowit | G01J 3/0251 250/226 |
| 6,113,578 A * | 9/2000 | Brown | A61B 5/14532 222/23 |
| 6,147,761 A * | 11/2000 | Walowit | G01J 3/0251 356/328 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 9,152,829 B2 * | 10/2015 | Day | A61M 5/20 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0040034 A1 * | 2/2007 | Hennick | G06K 7/10732 235/462.41 |
| 2008/0287865 A1 * | 11/2008 | Nielsen | A61M 5/3155 604/65 |
| 2009/0275916 A1 | 11/2009 | Harms et al. | |
| 2010/0286612 A1 * | 11/2010 | Cirillo | A61M 5/31525 604/111 |
| 2011/0000966 A1 | 1/2011 | Liu | |
| 2011/0238017 A1 | 9/2011 | Watanabe et al. | |
| 2012/0022458 A1 | 1/2012 | Oh et al. | |
| 2012/0043377 A1 * | 2/2012 | Haar | A61B 5/14532 235/375 |
| 2012/0215162 A1 * | 8/2012 | Nielsen | A61M 5/3155 604/65 |
| 2012/0323176 A1 * | 12/2012 | Watanabe | A61M 5/20 604/131 |
| 2013/0030405 A1 * | 1/2013 | Hartman | A61M 5/14228 604/500 |
| 2013/0072897 A1 | 3/2013 | Day et al. | |
| 2013/0197445 A1 * | 8/2013 | Schabbach | A61B 5/14532 604/189 |
| 2013/0221097 A1 * | 8/2013 | Day | A61M 5/20 235/437 |
| 2014/0207080 A1 * | 7/2014 | Allerdings | A61M 5/24 604/207 |
| 2015/0018775 A1 * | 1/2015 | Groeschke | A61M 5/24 604/207 |
| 2015/0025470 A1 * | 1/2015 | Baran | A61M 5/24 604/187 |
| 2015/0032059 A1 * | 1/2015 | Allerdings | G06F 19/3468 604/189 |
| 2015/0356273 A1 * | 12/2015 | Cave | A61M 5/24 705/2 |
| 2015/0367079 A1 * | 12/2015 | Steel | A61M 5/31525 604/207 |
| 2016/0047685 A1 * | 2/2016 | Blei | A61M 5/31551 250/227.11 |
| 2016/0051762 A1 * | 2/2016 | Allerdings | A61M 5/24 604/187 |
| 2017/0219486 A1 * | 8/2017 | Blei | G01N 21/3577 |

FOREIGN PATENT DOCUMENTS

| | | |
|---|---|---|
| EP | 0937471 A2 | 8/1999 |
| EP | 0937476 A2 | 8/1999 |
| JP | 2003-532944 | 11/2003 |
| WO | 9803215 A1 | 1/1998 |
| WO | WO 98/03215 | 1/1998 |
| WO | 9938554 A1 | 8/1999 |
| WO | 0110484 A1 | 2/2001 |
| WO | WO 2001/026036 | 4/2001 |
| WO | 2006120182 A1 | 11/2006 |
| WO | 2010128493 A2 | 11/2010 |
| WO | WO 2011/089205 | 7/2011 |
| WO | 2011117212 A1 | 9/2011 |
| WO | 2013004843 A1 | 1/2013 |

OTHER PUBLICATIONS

International Preliminary Report on Patentability in International Application No. PCT/EP2014/057774, dated Oct. 27, 2015, 8 pages.

* cited by examiner

SENSOR DEVICE FOR ATTACHMENT TO A DRUG DELIVERY DEVICE

CROSS REFERENCE TO RELATED APPLICATIONS

The present application is a U.S. National Phase Application pursuant to 35 U.S.C. § 371 of International Application No. PCT/EP2014/057774 filed Apr. 16, 2014, which claims priority to European Patent Application No. 13164746.3 filed Apr. 22, 2013. The entire disclosure contents of these applications are herewith incorporated by reference into the present application.

FIELD OF INVENTION

The present invention relates to a sensor device for attachment to a drug delivery device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

A first aspect of the invention provides a sensor device configured to be attached to a drug delivery device and configured to illuminate the drug delivery device when attached, the sensor device comprising:
  a light guide having a first surface, a second surface opposed to the first surface, at least one side surface extending between the first and second surfaces and a light out-coupling structure configured to cause diffuse light to be emitted from the first surface when light is input into the light guide;
  at least one light source configured to in-couple light into the light guide; and
  an optical sensor arranged to receive light reflected from a surface of the drug delivery device.

The sensor device may be configured to be releasably attached to a drug delivery device. The sensor device may alternatively be configured to be non-releasably attached to a drug delivery device.

The sensor device may be configured to illuminate the drug delivery device when attached. The sensor device may be configured to illuminate a surface portion of the drug delivery device when attached. The sensor device may cover a surface portion of the drug delivery device when attached. The sensor device may be configured to illuminate at least part of the covered surface portion of the drug delivery device when attached.

The use of a light guide to produce diffuse light is advantageous as the diffuse light which is emitted from the first surface provides even illumination of the surface of the object which is to be imaged by an optical sensor, e.g. a surface or surface portion of a drug delivery device. Reflections, bright spots and distortions which may hamper the image taking process are reduced or eliminated by the use of the light guide.

The at least one light source may in-couple light via the at least one side surface of the light guide. This arrangement keeps the light sources separated from the optical sensor. This arrangement also causes most of the input light to undergo total internal reflection within the light guide until encountering the out-coupling structure.

The light out-coupling structure may be part of the first surface. The light out-coupling structure may present a different surface aspect to incoming light which causes the light to be emitted from the light guide, rather than reflected internally.

The sensor device may further comprise a reflective backing layer adjacent the second surface configured to reflect any light which escapes the light guide through the second surface back into the light guide. This increases the illumination efficiency of the light guide and consequently the power efficiency of the sensor device.

The light guide may comprise a region without the light out-coupling structure. This allows the shape of the light emitting part of the light guide to be controlled. The optical sensor may be arranged, when the sensor device is attached to the drug delivery device, to view a predetermined area of the surface of the drug delivery device through the region without the light out-coupling structure. The predetermined area may have a feature such as a glyph, character, number, symbol, encoded image or other marking or surface feature. This allows the optical sensor to capture a clear image of the feature of the surface of the drug delivery device.

The region without the light out-coupling structure may comprise an unmodified region of the light guide. As a result, the optical sensor can clearly view the surface of the drug delivery device through the unmodified region while light within the light guide can pass through and be reflected internally.

The region without the light out-coupling structure may comprise a hole in the light guide. No visual distortion of the capture images results from this arrangement.

The sensor device may further comprise a lens assembly configured to focus light reflected from a surface of the drug delivery device onto the optical sensor. This increases the overall light intensity reflected to the sensor and thereby may improve signal to noise ratio. This may also reduce the technical requirement of the optical sensor, e.g. in terms of light intensity sensitivity and allow a cheaper sensor to be used.

The lens assembly may be disposed in the hole in the light guide such that a first end of the lens assembly is the same or a smaller distance from the surface of the drug delivery device than the first surface of the light guide. This may result in a space saving within the sensor device and/or reduce the cost and complexity of the optical elements in the lens assembly. This arrangement may also allow a lower level of illumination to be used as the lens assembly and optical sensor are closer to the surface of the drug delivery device. Unwanted distortion and reflection effects may also be mitigated by placing the lens assembly closer to the drug delivery device.

A sensor device according to the invention may further comprise an optical sensor and a processor configured to receive light intensity signals from the sensor and to perform an optical character recognition process on the received signals to determine a character such as a letter and/or number visible on the surface of an object which is to be imaged by an optical sensor, e.g. a surface or surface portion of a drug delivery device. The character may comprise a single letter, multiple letters, words, abbreviations as well as numbers of variable digit length, including decimals.

The sensor device may further comprise a processor configured to receive light intensity signals from the sensor and to perform an optical character recognition process on the received signals to determine characters such as letters and/or numbers visible on the surface of an object which is to be imaged by the optical sensor, e.g. a surface or surface portion of a drug delivery device. The character may comprise a single letter, multiple letters, words, abbreviations as well as numbers of variable digit length, including decimals.

The processor may be further configured to determine an amount of medicament dialled into the drug delivery device and to cause the amount of medicament to be displayed on a display device of the drug delivery device.

In order to improve illumination of an object, e.g. a drug delivery device, the first and/or second surfaces of the light guide may be curved. The curvature of the light guide, i.e. the first and/or second surface of the light guide may be such that when the sensor device is attached to the drug delivery device the curvature is adapted to the surface of the object to be illuminated. The curvature of the light guide may be such that when the sensor device is attached to the drug delivery device, the light emitting surface of the light guide and the surface of the drug delivery device are concentric or substantially concentric. The first surface of the light guide may be concentric or substantially concentric with the surface of the drug delivery device. The second surface of the light guide may also be concentric or substantially concentric with the surface of the drug delivery device. Thus, the distance between the light emitting surface and the light reflecting surface is approximately constant across the field of view of the optical sensor. This results in a more homogeneous illumination of the drug delivery device.

In order to improve illumination of an object, e.g. a drug delivery device, the sensor device may comprise at least one additional light guide and the light guide and additional light guides may be arranged such that none of the light guides obstruct the optical sensor's view of the surface of the drug delivery device. The light guide and the at least one additional light guide may be even. The light guide and the at least one additional light guide may be curved. The light guide and the at least one additional light guide may be oriented such that their respective surface normals meet in substabtially in one point. This point may be substantially in the centre of the object to be illuminated. The light guide and the at least one additional light guide may be oriented such that their respective surface normals span a line, in case of one additional light guide, or a polygon spot, in the case of more than one additional light guide, in a plane. The line or plane may be around the centre of the object to be illuminated.

The drug delivery device may be a pen type injection device and the surface of the drug delivery device may be a cylindrical surface.

A second aspect of the invention provides a system comprising the sensor device of the first aspect and a drug delivery device configured to be attached to the sensor device.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices as well as with other types of transcutaneous drug delivery devices and methods.

Figure 1A:
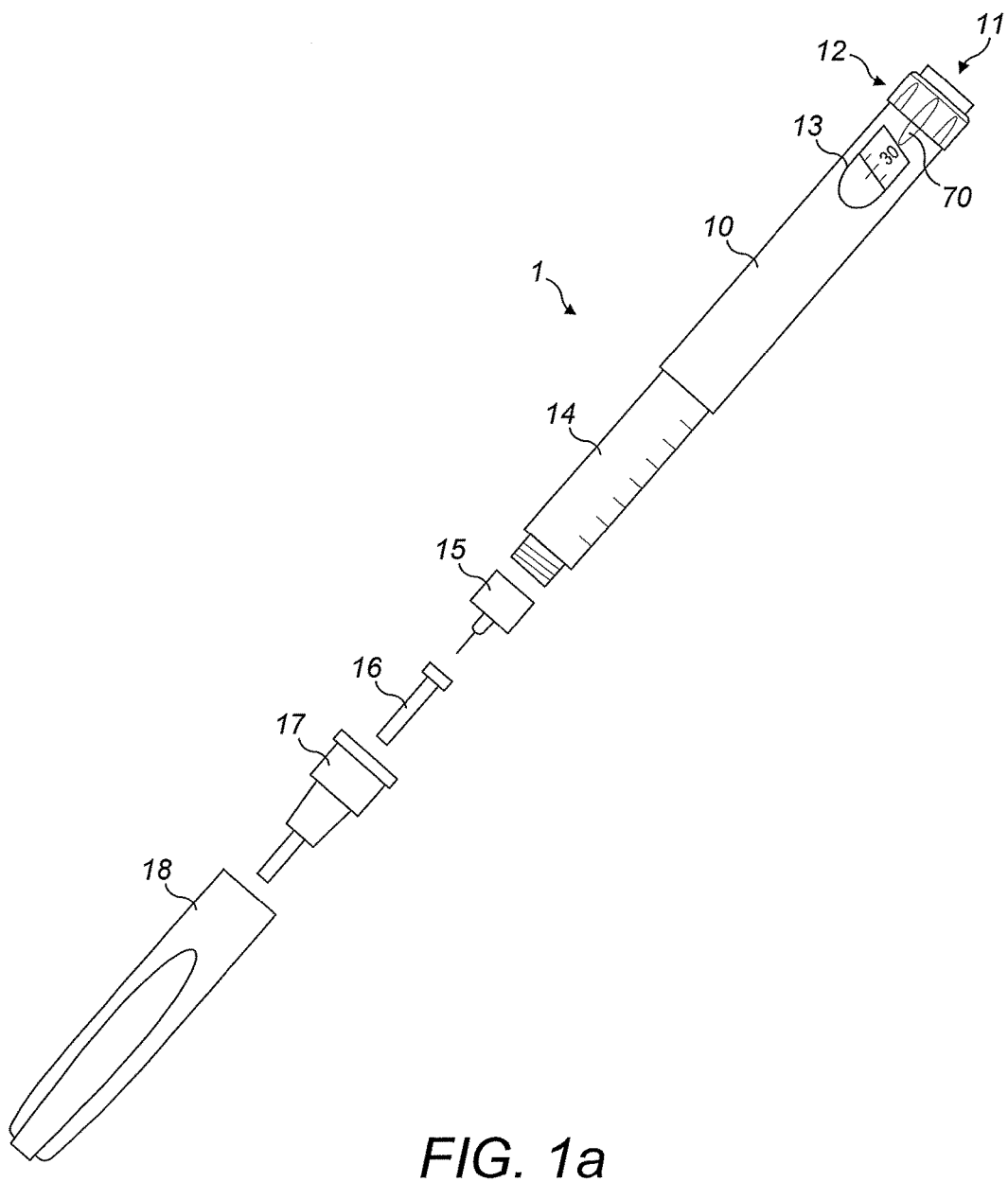
FIG. 1a: an exploded view of an drug delivery device.

FIG. 1a is an exploded view of a drug delivery device 1, which may for instance represent Sanofi's Solostar (R) insulin injection pen. The drug delivery device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from drug delivery device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently, for instance by means of an electronic display.

Figure 1B:
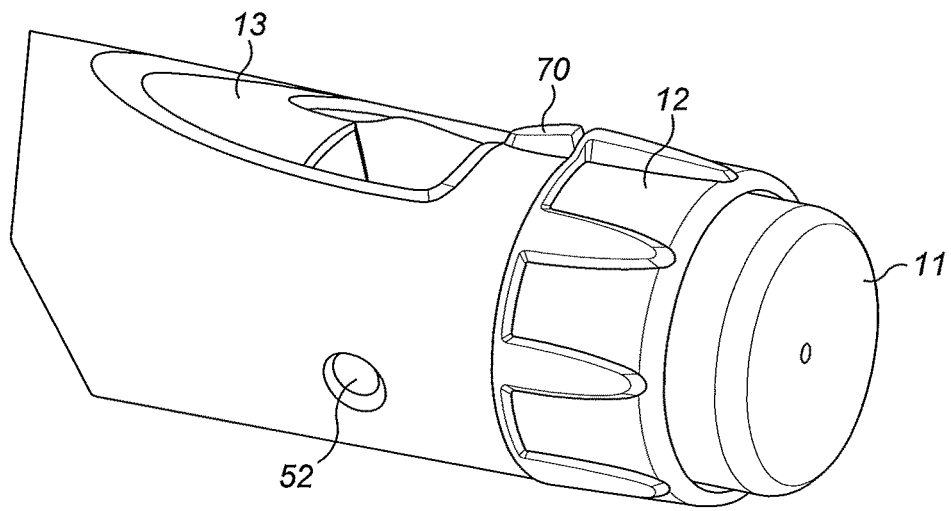
FIG. 1b shows a perspective view of some detail of the drug delivery device of FIG. 1.

FIG. 1b is a perspective view of the dosage knob 12 end of the drug delivery device 1. Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from drug delivery device 1. When the needle 15 of drug delivery device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

The housing 10 of the drug delivery device 1 may comprise locator features, such as one or more protrusions 70 and/or one or more indentations 52. These locator features allow a sensor device (described below) to be releasably attached to the drug delivery device 1 in an accurate predetermined position.

Drug delivery device 1 may be used for several injection processes until either insulin container 14 is empty or the expiration date of drug delivery device 1 (e.g. 28 days after the first use) is reached. Furthermore, before using drug delivery device 1 for the first time, it may be necessary to perform a so-called "prime shot" to remove air from insulin container 14 and needle 15, for instance by selecting two units of insulin and pressing injection button 11 while holding drug delivery device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the drug delivery device. Nevertheless, differences (e.g. losses) between the ejected doses and the injected doses may of course be taken into account.

Figure 2A:
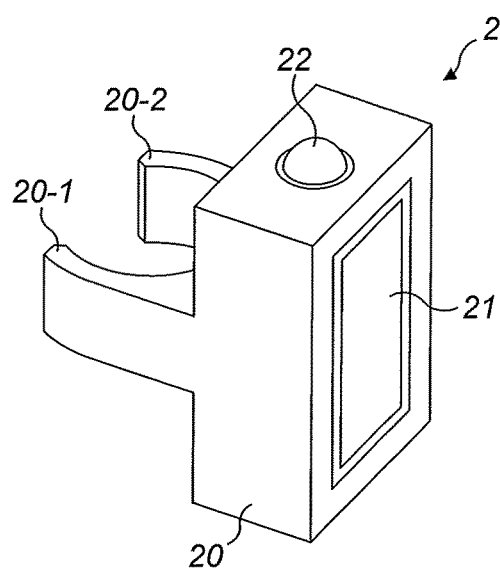
FIG. 2a: a schematic illustration of a sensor device to be releasably attached to the drug delivery device of FIG. 1 according to an aspect of the present invention.

FIG. 2a is a schematic illustration of an embodiment of a sensor device 2 to be releasably attached to drug delivery device 1 of FIG. 1. Sensor device 2 comprises a housing 20 with a mating unit configured and embrace the housing 10 of drug delivery device 1 of FIG. 1, so that sensor device 2 sits tightly on housing 10 of drug delivery device 1, but is nevertheless removable from drug delivery device 1, for instance when drug delivery device 1 is empty and has to be replaced. FIG. 2a is highly schematic, and details of the physical arrangement are described below with reference to FIG. 2b.

Sensor device 2 contains optical and optional acoustical sensors for gathering information from drug delivery device 1. Information is displayed via display unit 21 of sensor device 2. The dosage window 13 of drug delivery device 1 is obstructed by sensor device 2 when attached to drug delivery device 1. Sensor device 2 further comprises at least one input transducer, illustrated schematically as a button 22. These input transducers 22 allow a user to turn on/off sensor device 2, to trigger actions (for instance to cause establishment of a connection to or a pairing with another device, and/or to trigger transmission of information from sensor device 2 to another device), or to confirm something.

Figure 2B:
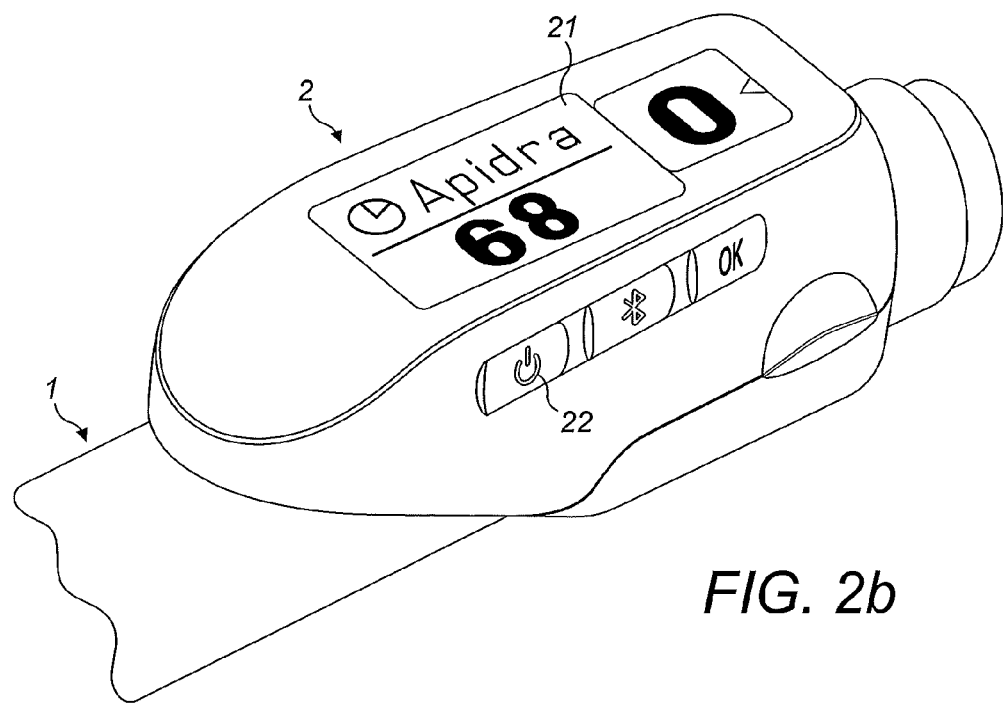
FIG. 2b: a perspective view of a sensor device to be releasably attached to the drug delivery device of FIG. 1 according to various aspects of the present invention.

FIG. 2b is a schematic illustration of a second embodiment of a sensor device 2 to be releasably attached to drug delivery device 1 of FIG. 1. Sensor device 2 comprises a housing 20 with a mating unit configured and embrace the housing 10 of drug delivery device 1 of FIG. 1, so that sensor device 2 sits tightly on housing 10 of drug delivery device 1, but is nevertheless removable from drug delivery device 1. The mating unit may engage with protrusion 70 and/or with indentations 52.

Information is displayed via display unit 21 of sensor device 2. The dosage window 13 of drug delivery device 1 is obstructed by sensor device 2 when attached to drug delivery device 1. Sensor device 2 further comprises three user input buttons or switches. A first button 22 is a power on/off button, via which the sensor device 2 may for instance be turned on and off. A second button 33 is a communications button. A third button 34 is a confirm or OK button. The buttons 22, 33, 34 may be any suitable form of mechanical switch. These input buttons 22 allow a user to turn on/off sensor device 2, to trigger actions (for instance to cause establishment of a connection to or a pairing with another device, and/or to trigger transmission of information from sensor device 2 to another device), or to confirm something.

Figure 2C:
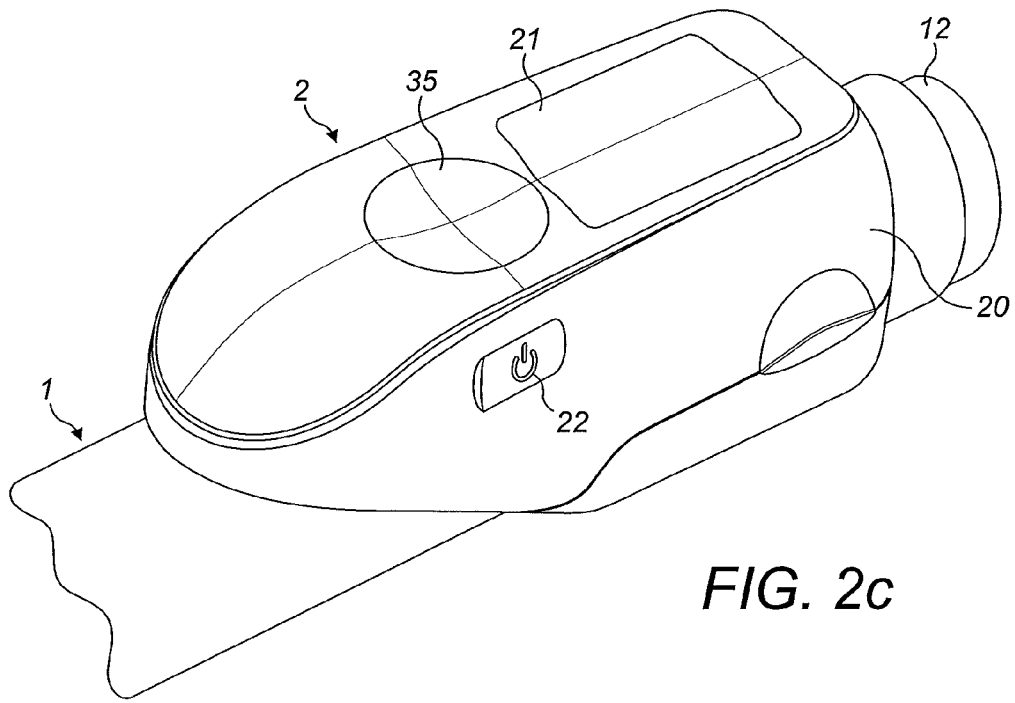
FIG. 2c: a perspective view of a sensor device to be releasably attached to the drug delivery device of FIG. 1 according to other aspects of the present invention.

FIG. 2c is a schematic illustration of a third embodiment of a sensor device 2 to be releasably attached to drug delivery device 1 of FIG. 1. Sensor device 2 comprises a housing 20 with a mating unit configured and embrace the housing 10 of drug delivery device 1 of FIG. 1, so that sensor device 2 sits tightly on housing 10 of drug delivery device 1, but is nevertheless removable from drug delivery device 1.

Information is displayed via display unit 21 of the sensor device 2. The dosage window 13 of drug delivery device 1 is obstructed by sensor device 2 when attached to drug delivery device 1. Sensor device 2 further comprises a touch-sensitive input transducer 35. It also comprises a single user input button or switch 22. The button 22 is a power on/off button, via which the sensor device 2 may for instance be turned on and off. The touch sensitive input transducer 35 can be used to trigger actions (for instance to cause establishment of a connection to or a pairing with another device, and/or to trigger transmission of information from sensor device 2 to another device), or to confirm something.

Figure 3:
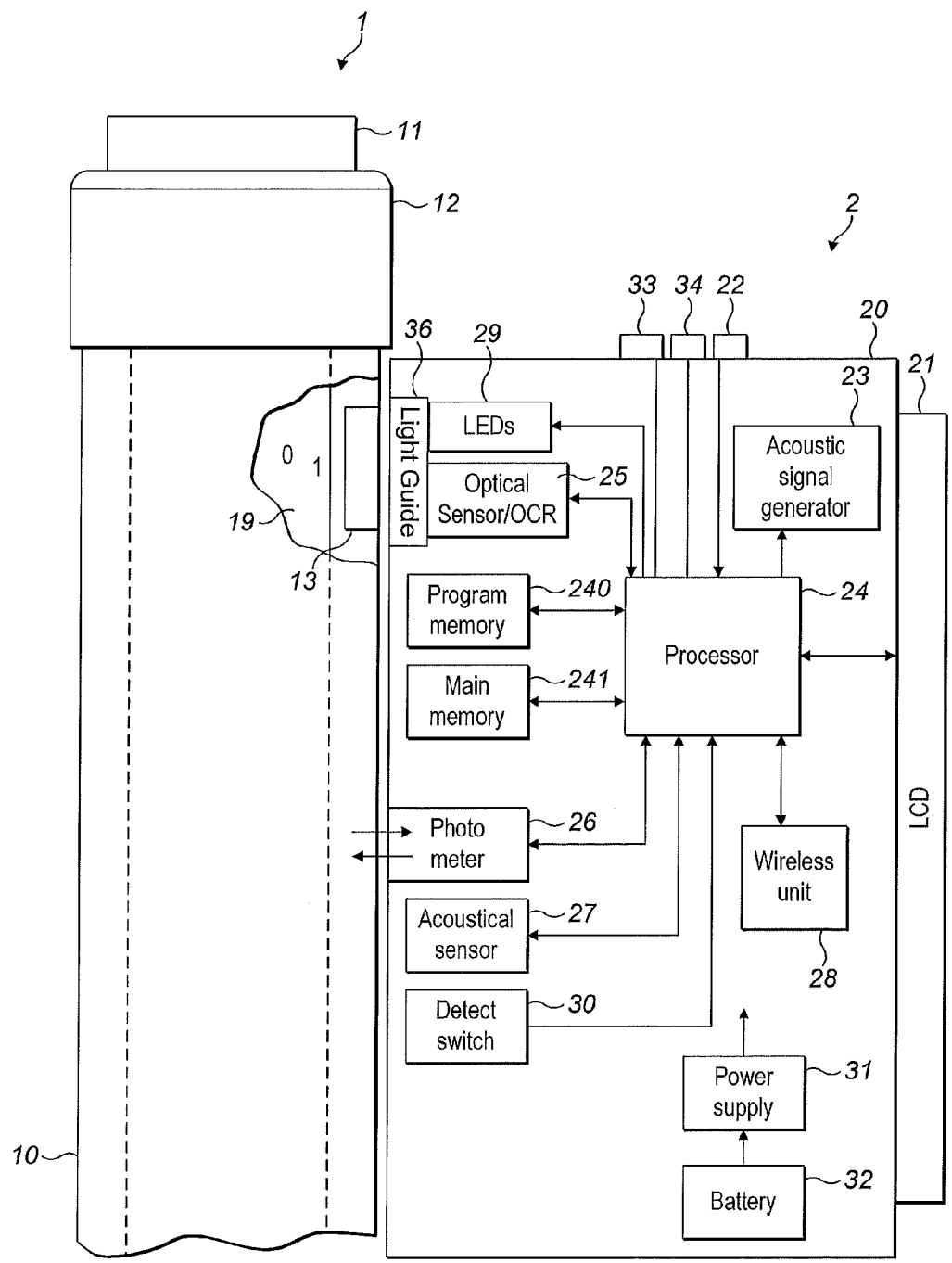
FIG. 3: a schematic view of a sensor device attached to an drug delivery device showing components of the sensor device.

FIG. 3 shows a schematic view of the sensor device 2 of FIG. 2a, 2b or 2c in a state where it is attached to drug delivery device 1 of FIG. 1.

A plurality of components are contained within the housing 20 of sensor device 2. The components of the sensor device 2 are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which sensor device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of sensor device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of sensor device 2, for instance on present settings of drug delivery device 1, or on a next injection to be given. Display unit 21 may also be embodied as a touch-screen display, for instance to receive user input.

Processor 24 also controls an optical sensor 25, also referred to herein as an optical sensor assembly 25. In some embodiments the optical sensor is a photosensitive device, such as a camera, for capturing images of the dosage window 13, in which a currently selected dose is displayed (by means of numbers printed on the sleeve 19 contained in drug delivery device 1, which numbers are visible through the dosage window 13) and providing information on the captured images to processor 24. Then processor 24 may then perform an Optical Character Recognition (OCR) process on the captured images. In some other embodiments, the optical sensor 25 is embodied as an OCR reader, that is capable of capturing images and recognizing characters (e.g. numbers) from the captured image and to provide this information to processor 24.

Processor 24 also controls light sources such as light emitting diodes (LEDs) 29. The LEDs 29 illuminate the dosage window 13 via a light guide 36, described in detail below. Furthermore, the sensor device 2 may comprise a lens (e.g. an aspheric lens) arranged in front of the optical sensor 25, leading to a magnification (e.g. a magnification of more than 3:1). The sensor device 2 may also comprise a transparent protection window (not shown) on the underside. The protection window prevents the ingress of dust and dirt into the sensor device 2. The light sources may be configured to illuminate the dosage window 13 through this protection window and the optical sensor 25 views the dosage window 13 through the protection window.

Processor 24 may further control a photometer 26, that is configured to determine an optical property of the housing 10 of drug delivery device 1, for example a colour or a shading. The optical property may only be present in a specific portion of housing 10, for example a colour or colour coding of sleeve 19 or of an insulin container comprised within drug delivery device 1, which colour or colour coding may for instance be visible through a further window in housing 10 (and/or in sleeve 19). Information on this colour is then provided to processor 24, which may then determine the type of drug delivery device 1 or the type of insulin contained in drug delivery device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by means of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the drug delivery device and/or the medicament contained therein. This code may for instance be located on the housing 10 or on a medicament container contained in drug delivery device 1, to name but a few examples. This code may for instance indicate a type of the drug delivery device and/or the medicament, and/or further properties (for instance a expiration date). The photometer 26 is an optional feature and may be omitted form the sensor device 2.

Processor 24 may further control (and/or receive signals from) an acoustic sensor 27, which is configured to sense sounds produced by drug delivery device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only). The acoustic sensor 27 is an optional feature and may be omitted form the sensor device 2.

Processor 24 may further control an acoustical signal generator 23, which is configured to produce acoustical signals that may for instance be related to the operating status of drug delivery device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by means of vibration. The acoustical signal generator 23 is an optional feature and may be omitted form the sensor device 2.

Processor 24 may control a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. In some other embodiments, no means for removing data from the sensor device 2 are provided.

Processor 24 receives an input from a pen detection switch 30, which is operable to detect whether the pen 1 is present, i.e. to detect whether the sensor device 2 is coupled to the drug delivery device 1. The pen detection switch 30 is an optional feature. A battery 32 powers the processor 24 and other components by way of a power supply 31.

Processor 24 may be configured to receive two input signals and derive from that whether the sensor device 2 is coupled to the drug delivery device 1. The input signals may be provided by any sensor, in particular any of the input sensors mentioned before, such as acoustic sensor 27, optical sensor 25, or photometer 26. For example, the input signal may be provided by a photometer 26, that is configured to determine an optical property of the housing 10 of drug delivery device 1, for example a colour or a shading. Or alternatively, the input signal may be provided by an optical sensor 25, also referred to herein as an optical sensor assembly 25, wherein the optical sensor is a photosensitive device, such as a camera, for capturing images of the dosage window 13, in which a currently selected dose is displayed. Further alternatively, the processor 24 may receive a combination of two different input signals, e.g. one input signal provided by a photometer 26 and another input signal provided by an optical sensor 25. Other combinations are also feasible, such as input signals from a photometer 26 and an acoustic sensor 27, input signals from an optical sensor 25 and an acoustic sensor 27.

The sensor device 2 of FIG. 3 is thus capable of determining information related to a condition and/or use of drug delivery device 1. This information is displayed on the display 21 for use by the user of the device. The information may be either processed by sensor device 2 itself, or may at least partially be provided to another device (e.g. a blood glucose monitoring system).

The processor 24 constitutes a processor arrangement. The optical sensor/OCR reader 25 and the processor 24 together constitute a dose dialled detector operable to detect a dose of medicament dialled and may also constitutes a dose delivery determiner for determining that a dose of medicament has been delivered and the quantity of the delivered dose. The processor 24 provides a function of a clock configured to determine a current time.

Figure 4:
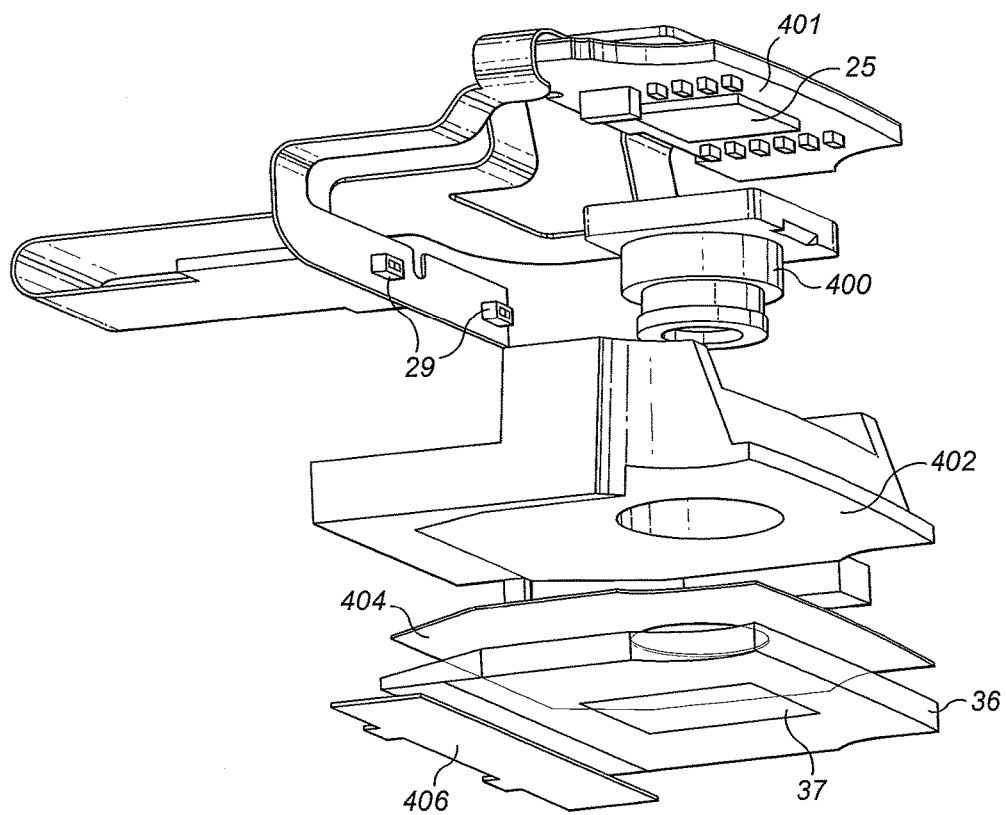
FIG. 4: an exploded view of some components of the sensor device according to embodiments of the invention.

FIG. 4 is an exploded view of some components of the sensor device 2 according to embodiments of the invention, including the optical sensor 25 and light guide 36 parts. The optical sensor 25 may be a matrix sensor comprising an array of light sensitive elements each capable of measuring the intensity of incident light. The matrix sensor may be a monochrome sensor. The optical sensor 25 is mounted on a printed circuit board (PCB) 401.

A lens assembly 400 may be mounted in front of the optical sensor 25. The focus of the lens assembly 400 may be adjustable. For example, the lens assembly 400 may be provided in two parts which are threadably engaged such that rotation of one part causes movement of an optical element along an optical axis. Both the lens assembly 400 and optical sensor 25 may be mounted on the same PCB 401. The lens assembly 400 may provide magnification of incident light onto the optical sensor 25. In some embodiments a lens assembly 400 is not needed and can be omitted.

Also mounted on the PCB 401 are two LEDs 29. The LEDs 29 are arranged so as to in-couple light into the light guide 36 via a side surface of the light guide. The LEDs 29 may therefore be supported on a part of the PCB 401 which is perpendicular to the part supporting the optical sensor 25. Generally at least two LEDs 29 are preferable in order to provide an even illumination, however the sensor device 2 may be configured to operate with only one LED 29. In other embodiments more than two LEDs 29 are provided. The LEDs 29 may in-couple light via two or more sides of the light guide 36 and the PCB 401 may be extended accordingly to support LEDs on two or more sides of the light guide.

FIG. 4 also shows an internal carrier member 402 located between the optical sensor 25 and the light guide 36. The internal carrier member 402 may serve several purposes, such as to protect and support the PCB 401, optical sensor 25, lens assembly 400 and other hardware components of the sensor device 2. The internal carrier member 402 may also ensure correct separation distance between the optical sensor 25 and external housing 20 of the sensor device 2 and block any light from reaching the optical sensor 25 directly from the LEDs 29. The internal carrier member 402 has a hole arranged to receive the lens assembly 400 (if present) and to allow light reflected from the surface of the drug delivery device 1 to enter the sensor device 2 and be received by the optical sensor 25.

The light guide 36 is a transparent piece of material, e.g. glass or a plastic. The light guide 36 has a lower surface, which is visible when the sensor device 2 is viewed from the underside and through which light is out-coupled towards the drug delivery device 1 when the sensor device 2 is in use. The light guide 36 has an upper surface, opposed to the lower surface, which faces the internal carrier member 402. A reflective layer 404 may be disposed between the upper surface of the light guide 36 and the internal carrier member 402. This reflective layer 404 ensures that any light which escapes the light guide 36 through the upper surface is reflected back into the light guide 36. The reflective layer 404 may be a mirror foil. The reflective layer 404 has a hole aligned with the hole in the internal carrier member 402 in order to allow light reflected from the surface of the drug delivery device 1 to enter the sensor device 2 and be received by the optical sensor 25. In some other embodiments, the reflective layer 404 may be adhered to the internal carrier member 402 or the internal carrier member 402 may be coated with a reflective layer.

The light guide 36 has at least one side surface joining the upper and lower surfaces. For example, the light guide 36 may be substantially square or rectangular in shape with four side surfaces. Light is in-coupled to the light guide 36 from the LEDs 29 via the side surfaces. Regions of the side surfaces which do not have LEDs 29 may have a reflective layer, or the reflective layer 404 may be extended to cover these side surfaces. The thickness of the light guide 36 may be reduced along the length of the side(s) at which the LEDs 29 are located and a section of the light guide may be tapered. This may be done to match the thickness of the light guide 36 to the size of the LEDs 29.

A guard member 406 may be placed against the lower surface of the light guide 36 in the region nearest the side(s) at which the LEDs 29 in-couple the light. In general, the input light spreads and becomes more homogeneous as it propagates through the light guide 36. However, light which escapes the light guide near the points at which the light is input may still resemble point sources. The guard member 406 acts to block the escape of light until it is sufficiently diffuse.

In order to facilitate the emission of diffuse light from the lower surface of the light guide 36, the light guide comprises an out-coupling structure. This out-coupling structure may take a variety of forms and may be transmissive or reflective. For example, the out-coupling structure may be a part of the lower surface of the light guide and may comprise a rough surface. The rough surface may be continuous or arranged into a number of discreet areas. Alternatively the lower surface of the light guide 36 may comprise rounded segments, microdots or prisms or regions of different refractive index. The light out-coupling structures may be distributed evenly across the lower surface of the light guide 36. Alternatively, the light out-coupling structures may be unevenly distributed, for example by becoming denser or sparser with increasing distance from the light input points. This may result in a more even distribution of light output. The effect of this light guide structure is that most light rays are contained within the light guide 36 either by total internal reflection when incident on the upper surface, a flat part of the lower surface, or by being reflected back into the light guide by the reflective layer 404. The out-coupling structure presents a different surface angle or different refractive index boundary to an incident light ray, causing the light ray to be emitted from the lower surface.

The light guide comprises a region 37 without any light out-coupling structure. This region 37 is arranged underneath the holes in the internal carrier member 402 and reflective layer 404 so as to be aligned with the lens assembly 400 (if present) and optical sensor 25. An effect of this region 37 is to allow the optical sensor 25 to view the part of the drug delivery device 1 which is illuminated and to capture an image of the drug delivery device 1 which is not distorted or blurred by the light out-coupling structure. The region 37 without any light out-coupling structure may be any suitable shape, such as square, rectangular (as shown in FIG. 4), any other regular polygon, circular, oval or a mixture of straight and curved edges. A section of the light guide 36 closest to the LED input points may also have no light out-coupling structure. This section may correspond to the tapered section of the light guide 36 and may be covered by the guard member 406.

A number of different arrangement of the light guide 36 and region 37 without any light out-coupling structure may be used, as will now be described with reference to FIGS. 5A to 9. In these Figures, like numerals are used for like parts, and these parts are not described again in detail.

Figure 5A:
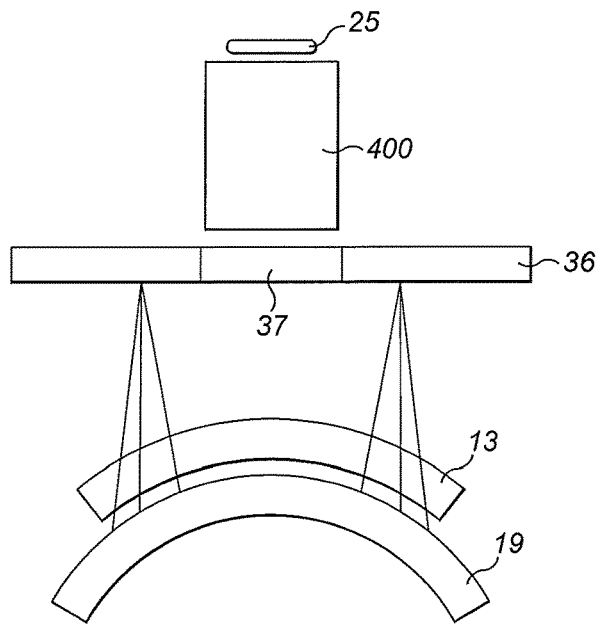
FIG. 5a: a schematic cross-sectional view of parts of the sensor device and drug delivery device according to embodiments of the invention.

FIG. 5A is a schematic cross-section view showing an arrangement similar to that of FIG. 4. The internal carrier member 402, LEDs 29, reflective layer 404 and other components are omitted for clarity. FIG. 5A shows the optical sensor 25 and lens assembly 400 positioned above the light guide 36. The light guide 36 of FIG. 5A is a planar black having upper and lower surfaces which are flat and parallel to each other. The region 37 without any light out-coupling structure is located directly underneath the lens assembly 400.

Diffuse light is emitted from the regions of the light guide 36 having the light out-coupling structure when the LEDs 29 (not shown) are active. This light passes through the dosage window 13 and illuminates the number sleeve 19 of the drug delivery device 1. Light reflected from the number sleeve 19 passed through the region 37 without any light out-coupling structure, through the lens assembly 400 and is received by the optical sensor 25. The optical sensor 25 then sends signals to the processor 24.

Figure 5B:
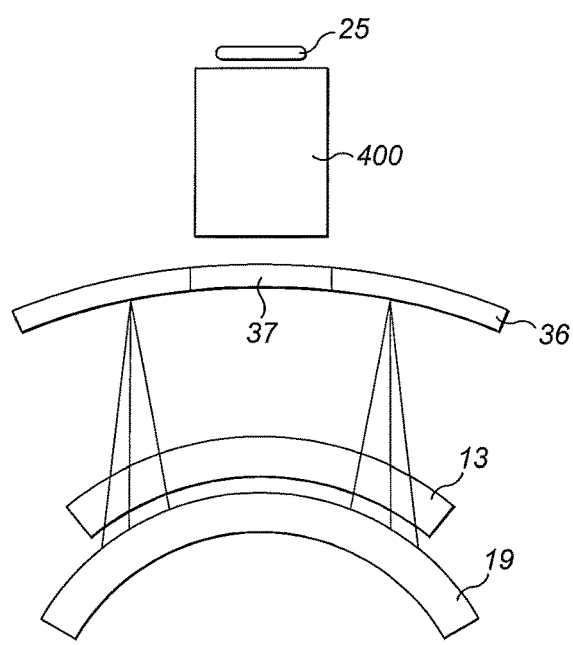
FIG. 5b: a schematic cross-sectional view of parts of the sensor device and drug delivery device according to further embodiments of the invention.

FIG. 5B shows another embodiment of the sensor device 2 in which the light guide 36 is curved. Having a curved light guide 36 increases the evenness of the illumination of the number sleeve 19, as the number sleeve has a cylindrical surface. Having a curved light guide 36 may also reduce reflections from the dosage window 13 and protection window (if present), therefore increasing the efficiency of the illumination. Preferably, the curvature of the light guide 36 is such that it is concentric with the number sleeve 19 and/or dosage window 13 when the sensor device 2 is attached to the drug delivery device 1. In some other embodiments, instead of a smooth curve, the light guide 36 may have a number of discreet changes in aspect.

Figure 6:
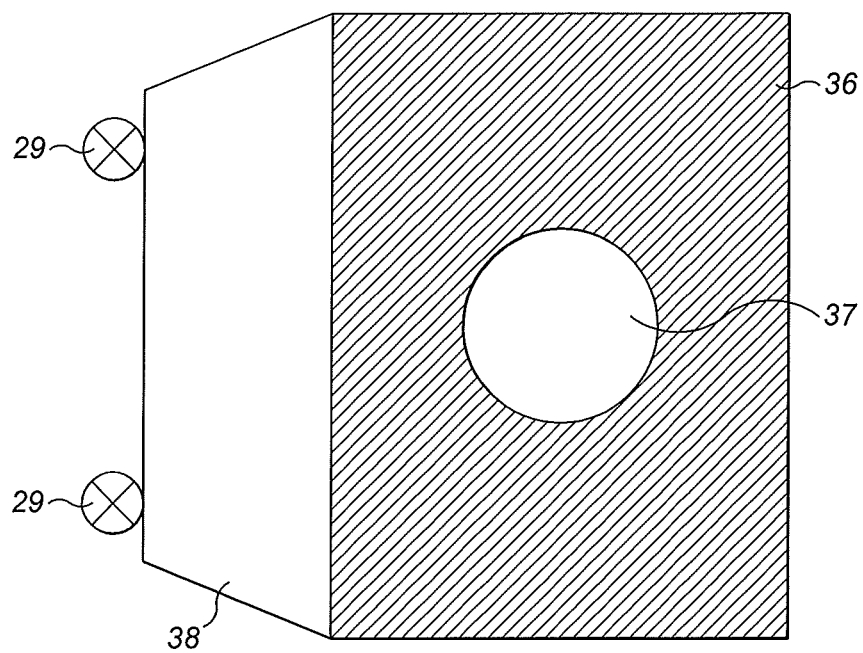
FIG. 6: a plan view of a light guide suitable for use in embodiments of the present invention.

FIG. 6 is a plan view of a light guide 36 suitable for use in embodiments of the present invention. The lower surface of the light guide 36 has a light out-coupling structure, represented by dots. A circular region 37 without any light out-coupling structure is provided approximately centrally in the light guide. This region 37 may comprise a section of the light guide 36 which is made of the same material, but which lacks any out-coupling structure. Alternatively, the region 37 may be made of a transparent material having different optical properties, such as a different refractive index. In some other embodiments, this region 37 comprises a hole in the light guide 36, i.e. the region 37 is comprised of air. Although a circular region 37 is shown, any suitable shape may be used, such as square, rectangular, any other regular polygon, oval or a mixture of straight and curved edges. LEDs 29 are arranged to in-couple light to the light guide 36 at one edge of the light guide. The region 38 of the light guide 36 adjacent the light input edge may be tapered, in thickness and/or in width (as shown in FIG. 6). This region 38 of the light guide may also lack any light out-coupling structure as the light propagating in this region may not yet be sufficiently homogeneous to provide even illumination. The light guide of FIG. 6 may be a planar plate, or may be curved as shown in FIGS. 5A and 5B respectively.

Figure 7:
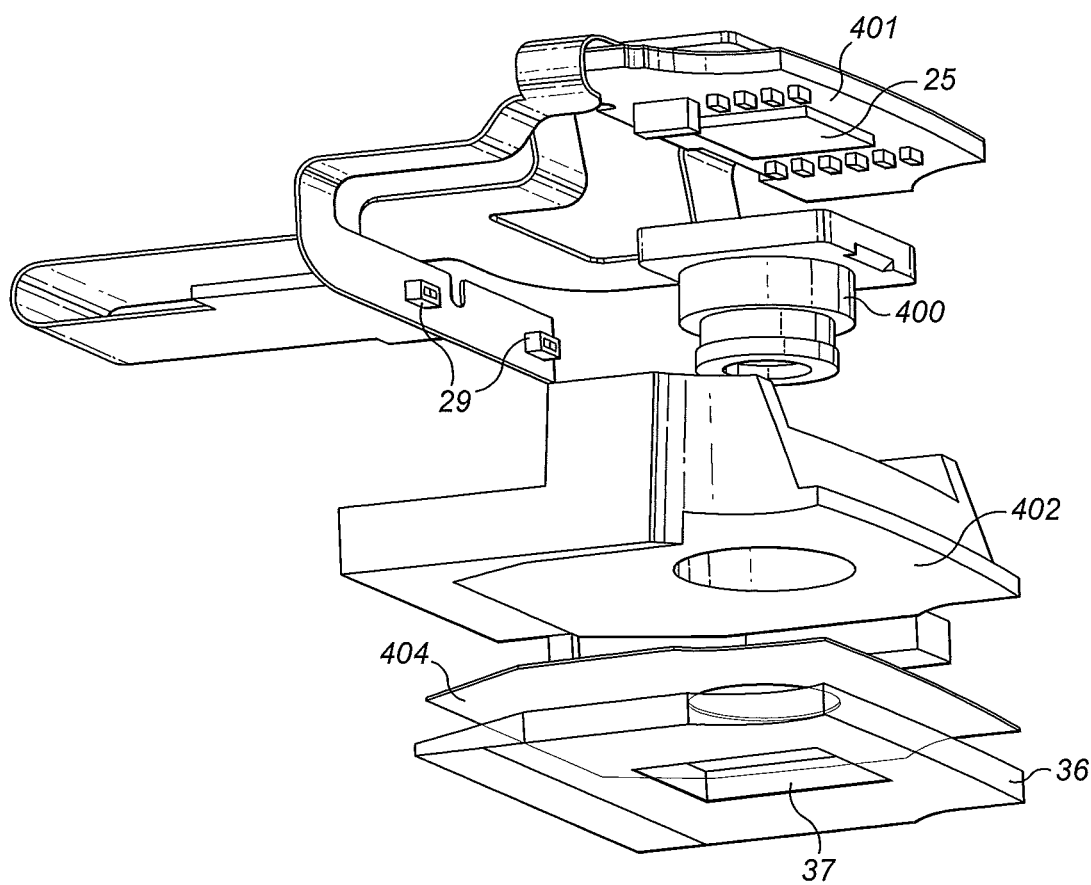
FIG. 7: an exploded view of some components of the sensor device according to embodiments of the invention.

FIG. 7 is an exploded view of some components of the sensor device 2 according to embodiments of the invention. FIG. 7 comprises the same components as described above with reference to FIG. 4. The light guide 36 shown in FIG. 7 has a region 37 without any light out-coupling structure which is comprised of a hole in the light guide. Providing a hole 37 in the light guide 36 has advantages over the transparent region shown in FIG. 4, in that there is zero distortion of the reflected light which passes through the hole 37. Depending on the method of manufacture, this light guide 36 may also be easier and cheaper to make. However, the hole 37 can lead to unwanted reflections within the light guide 36 which may reduce the evenness of the resulting illumination. Furthermore, using a transparent piece of material for the region 37 increases the efficiency of the illumination as light can propagate through and undergo total internal reflection within this region 37. Thus the power requirements of the sensor device 2 may be reduced while providing the same illumination brightness relative to a light guide with a hole.

Figure 8:
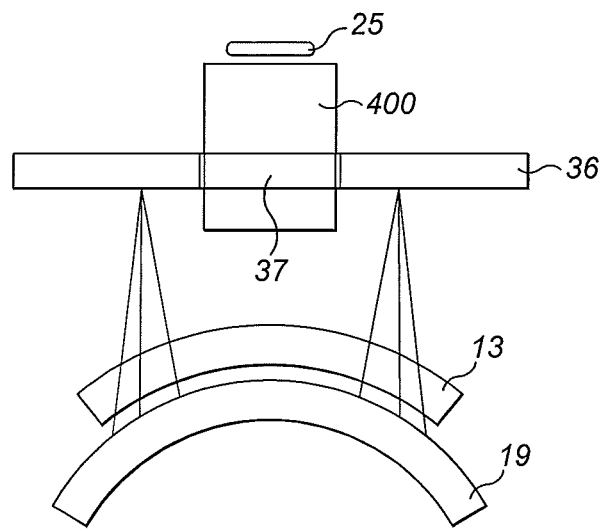
FIG. 8: a schematic cross-sectional view of parts of the sensor device and drug delivery device according to further embodiments of the invention.
Figure 9:
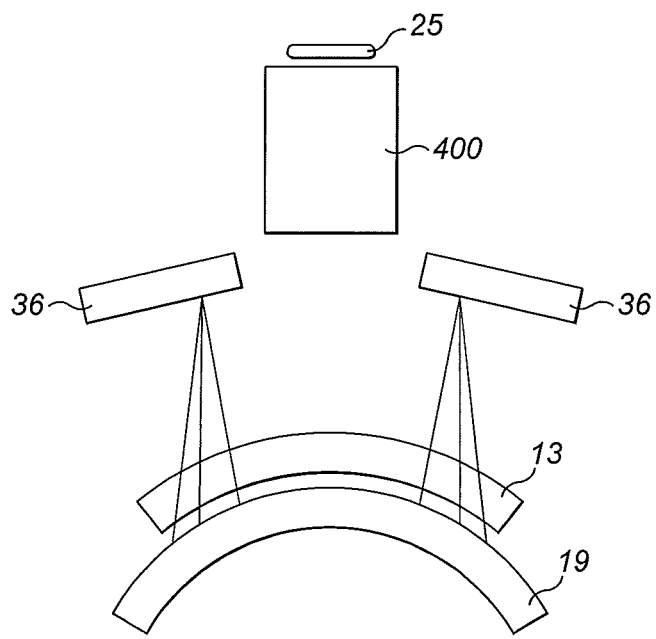
FIG. 9: a schematic cross-sectional view of parts of the sensor device and drug delivery device according to further embodiments of the invention.

FIGS. 8 and 9 show in schematic cross-section two further embodiments of the sensor device 2. In FIG. 8, the hole in the light guide 36 is large enough to accommodate the lens assembly 400. This may result in a space saving within the sensor device 2 and/or reduce the cost and complexity of the optical elements in the lens assembly. This arrangement may also allow a lower level of illumination to be used as the lens assembly 400 and optical sensor 25 are closer to the surface of the number sleeve 19. Unwanted distortion and reflection effects produced by the dosage window 13 and by the protection window (if present) may also be mitigated by placing the lens assembly 400 and optical sensor 25 closer to the window 13.

In FIG. 9, two light guides 36 are provided. In general, any number of light guides may be used to illuminate the number sleeve 19. Each light guide has respective LEDs (not shown) which in-couple light. An advantage of using multiple light guides 36 is that these light guides may be positioned and orientated in such a way as to better and more evenly illuminate the number sleeve 19 while reducing the amount of reflection effects produced by the dosage window 13 in a way that could not be achieved using a single light guide. The lens assembly 400 is positioned so that its view of the characters printed on the number sleeve 19 is not obstructed by any of the light guides 36.

Figure 10:
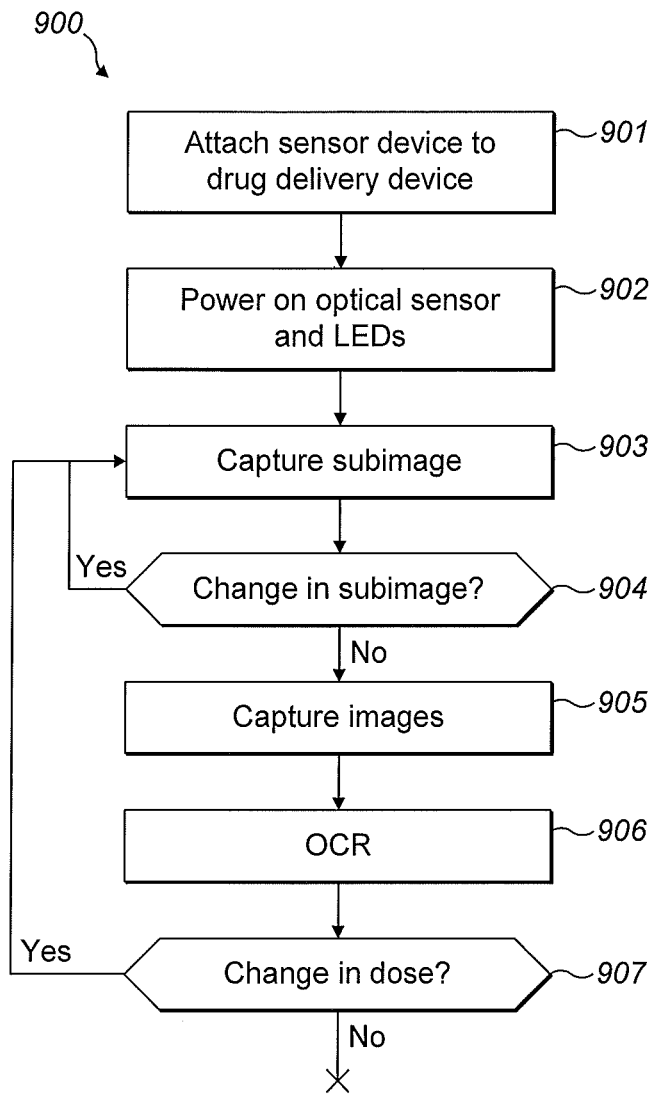
FIG. 10: a flowchart of a method used in various aspects.

FIG. 10 is a flowchart 900 of a method in which the present invention is embodied. In step 901, a user attaches the sensor device 2 to the drug delivery device 1. The pen detection switch 30 (if present) detects that the sensor device 2 has been attached to the drug delivery device 1. This may cause the sensor device 2 to be powered on. Alternatively, or if the detect switch 30 is not present, the user presses the power button 22 to switch the sensor device on. At this time the LEDs 29 and optical sensor 25 are also powered on (step 902).

The processor 24 of sensor device 2 may then execute a program stored in program memory 240 to determine a dose which is dialled into the drug delivery device 1 to which the sensor device is attached.

In a step 903, a sub-image is captured by an optical sensor such as optical sensor 25 of sensor device 2. The captured sub-image is for instance an image of at least a part of the dosage window 13 of drug delivery device 1, in which a currently selected dose is displayed (e.g. by means of numbers and/or a scale printed on the sleeve 19 of drug delivery device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of drug delivery device 1 which is visible through dosage window 13. The LEDs 29 which cause illumination of the number sleeve 19 may be operated in a dimmer and therefore lower power mode for the purpose of sub-image capture. After capturing an image, it is, for instance, further processed as follows:

Division by a previously captured background image;

Binning of the image(s) to reduce the number of pixels for further evaluations;

Normalization of the image(s) to reduce intensity variations in the illumination;

Sheering of the image(s); and/or

Binarization of the image(s) by comparing to a fixed threshold.

Several or all of these steps may be omitted if applicable, for instance if a sufficiently large optical sensor (e.g. a sensor with sufficiently large pixels) is used.

In a step 904, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 903 and 904 may correspond to a detection of a change in the captured image.

If it is determined in step 904 that there is a change in the sub-image, step 903 is repeated. Otherwise in a step 905, an image is captured by an optical sensor such as optical sensor 25 of sensor device 2. The captured image is for instance an image of the dosage window 13 of drug delivery device 1, in which a currently selected dose is displayed (e.g. by means of numbers and/or a scale printed on the sleeve 19 of drug delivery device 1, which is visible through the dosage window 13). For instance, the captured image may have a resolution being higher than the resolution of the captured sub-image. The captured image at least shows the numbers printed on the sleeve 19 of drug delivery device 1 which are visible through the dosage window 13.

In a step 906, optical character recognition (OCR) is performed on the image captured in step 905 in order to recognize the numbers printed on the sleeve 19 of drug delivery device 1 and visible through the dosage window 13, because these numbers correspond to the (currently) selected dose. This step may be performed by the optical sensor 25 if it is so programmed, or alternatively the optical sensor 25 may send signals representing light intensity values to the processor 24 and the processor may then perform the OCR process. In accord to the recognized numbers, the selected dose is determined, for instance by setting a value representing the selected dose to the recognized numbers.

In a step 907, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

A standard drug delivery device 1, in particular an insulin device, may be connected with a blood glucose monitoring system in a useful and productive way. The sensor device 2 may provide this connection, assuming the blood glucose monitoring system has wireless or other communication capabilities. The benefits from the connection between the blood glucose monitoring and an insulin drug delivery device are inter alia the reduction of mistakes by the user of the drug delivery device and a reduction of handling steps— no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the sensor device 2 to the pen. The sensor device reads out the injected dose. It may also transfer it to a blood glucose monitoring system with insulin titration capabilities. For patients taking multiple insulins, the sensor device 2 recognizes the device structure to the insulin type and may also transmit this piece of information to the blood glucose monitoring system.

In example embodiments, the information shown on a display, for example LCD display 21 of FIGS. 2*a-c* and 3, may also be converted to a sound signal played to a user through a speaker, for example by a text-to-speech functionality implemented by processor 24 using the acoustical signal generator 23. Thus, a user with impaired vision may have improved access to the information of sensor device 2, such as a dialled dose, a recommended dose, a recommended time for administration and/or the like.

When using embodiments of the present invention, the user inter alia has the following advantages:

The user can use the most convenient disposable insulin injector.

The sensor device is attachable and detachable (reusable).

Injected dose information may be transferred to the blood glucose monitoring system automatically (no more transfer mistakes). Improved dose guidance may result from this as the blood glucose monitoring system calculates the dose to be taken.

Keeping of a manual data logbook may not be needed any more.

Furthermore, when deploying the sensor device proposed by the present invention, patients may also be reminded of injecting their next dose by receiving an alarm signal, for instance, after an appropriate time after a first dose of a medicament (for instance insulin or heparin) has been injected.

Injected dose information may be transferred to any computerized system, for instance as input for any dose calculation or any other applicable therapeutic guidance calculation, or for the creation of an alarm signal, for instance to remind the user of taking the next dose.

The invention claimed is:

1. A sensor device configured to be attached to a drug delivery device and configured to illuminate the drug delivery device when attached, the sensor device comprising:
    a light guide having a first surface, a second surface opposed to the first surface, at least one side surface extending between the first and the second surfaces and a light out-coupling structure configured to cause diffuse light to be emitted from the first surface when light is input into the light guide;
    at least one light source configured to in-couple light into the light guide; and
    an optical sensor arranged to receive light reflected from a surface of the drug delivery device,
    wherein the sensor device further comprises a reflective backing layer adjacent the second surface configured to reflect any light which escapes the light guide through the second surface back into the light guide.

2. The sensor device according to claim 1, wherein the light out-coupling structure is part of the first surface.

3. The sensor device according to claim 1, wherein the light guide comprises a region without the light out-coupling structure.

4. The sensor device according to claim 3, wherein the optical sensor is arranged, when the sensor device is attached to the drug delivery device, to view a predetermined area of the surface of the drug delivery device through the region without the light out-coupling structure.

5. The sensor device according to claim 3, wherein the region without the light out-coupling structure comprises an unmodified region of the light guide.

6. The sensor device according to claim 3, wherein the region without the light out-coupling structure comprises a hole in the light guide.

7. The sensor device according to claim 6, wherein the sensor device further comprises a lens assembly configured to focus light reflected from a surface of the drug delivery device onto the optical sensor.

8. The sensor device according to claim 7, wherein the lens assembly is disposed in the hole in the light guide such that a first end of the lens assembly is the same or a smaller distance from the surface of the drug delivery device than the first surface of the light guide.

9. The sensor device according to claim 1, wherein the sensor device further comprises a processor configured to receive light intensity signals from the optical sensor and to perform an optical character recognition process on the received signals to determine a character visible on the surface of the drug delivery device.

10. The sensor device according to claim 9, wherein the processor is further configured to determine an amount of medicament dialled into the drug delivery device and to cause the amount of medicament to be displayed on a display device of the drug delivery device.

11. The sensor device according to claim 1, wherein the first and the second surfaces of the light guide are curved.

12. The sensor device according to claim 11, wherein the first and the second surfaces of the light guide are substantially concentric with the surface of the drug delivery device.

13. The sensor device according to claim 1, wherein the sensor device comprises at least one additional light guide and wherein the light guide and the at least one additional light guide are arranged such that none of the light guide and the at least one additional light guide obstructs the optical sensor's view of the surface of the drug delivery device.

14. The sensor device according to claim 9, wherein the character includes at least one of a letter and a number.

* * * * *